US010517885B2

(12) United States Patent
Lopes Da Silva (10) Patent No.: US 10,517,885 B2
(45) Date of Patent: Dec. 31, 2019

(54) PYRIMIDINE DERIVATIVE AND A FATTY ACID SOURCE FOR USE IN THE TREATMENT OF CONSTIPATION

(71) Applicant: N. V. Nutricia, Zoetermeer (NL)

(72) Inventor: Sofia Lopes Da Silva, Bunnik (NL)

(73) Assignee: N. V. Nutricia, Zoetermeer (NL)

( * ) Notice: Subject to any disclaimer, the term of this patent is extended or adjusted under 35 U.S.C. 154(b) by 4 days.

(21) Appl. No.: 15/102,136

(22) PCT Filed: Sep. 30, 2014

(86) PCT No.: PCT/NL2014/050671
§ 371 (c)(1),
(2) Date: Jun. 6, 2016

(87) PCT Pub. No.: WO2015/084160
PCT Pub. Date: Nov. 6, 2015

(65) Prior Publication Data
US 2016/0303159 A1    Oct. 20, 2016

(30) Foreign Application Priority Data
Dec. 6, 2013  (WO) ................ PCT/NL2013/050879

(51) Int. Cl.
| | | |
|---|---|---|
| *A61K 31/7072* | (2006.01) |
| *A61K 45/06* | (2006.01) |
| *A61K 31/14* | (2006.01) |
| *A61K 31/202* | (2006.01) |
| *A61K 31/355* | (2006.01) |
| *A61K 31/375* | (2006.01) |
| *A61K 31/4415* | (2006.01) |
| *A61K 31/519* | (2006.01) |
| *A61K 31/7068* | (2006.01) |
| *A61K 31/714* | (2006.01) |
| *A61K 33/04* | (2006.01) |
| *A23L 33/10* | (2016.01) |
| *A23L 33/15* | (2016.01) |
| *A61K 31/683* | (2006.01) |
| *A23L 33/12* | (2016.01) |
| *A23L 33/175* | (2016.01) |
| *A61K 9/00* | (2006.01) |
| *A61K 31/593* | (2006.01) |
| *A61K 31/715* | (2006.01) |
| *A61K 38/16* | (2006.01) |

(52) U.S. Cl.
CPC .......... *A61K 31/7072* (2013.01); *A23L 33/10* (2016.08); *A23L 33/12* (2016.08); *A23L 33/15* (2016.08); *A23L 33/175* (2016.08); *A61K 9/0053* (2013.01); *A61K 31/14* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/593* (2013.01); *A61K 31/683* (2013.01); *A61K 31/7068* (2013.01); *A61K 31/714* (2013.01); *A61K 31/715* (2013.01); *A61K 33/04* (2013.01); *A61K 38/16* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,017,550 A | * | 1/2000 | Berk ....................... | A23L 33/40 424/401 |
| 8,541,448 B2 | * | 9/2013 | Charmot ................ | A61K 31/18 514/307 |
| 2007/0015789 A1 | * | 1/2007 | Barth ..................... | A61K 31/46 514/304 |
| 2010/0234286 A1 | * | 9/2010 | Georgi .................... | A23L 1/296 514/5.5 |
| 2011/0118204 A1 | * | 5/2011 | Frauchiger .............. | A23L 33/40 514/47 |
| 2013/0189398 A1 | | 7/2013 | Rosado Loria et al. | |
| 2015/0216806 A1 | * | 8/2015 | Borody ................ | A61K 35/741 424/456 |

FOREIGN PATENT DOCUMENTS

| | | |
|---|---|---|
| EP | 2143340 A1 | 1/2010 |
| WO | 98/06277 A1 | 2/1998 |

OTHER PUBLICATIONS

Olanow, C. W., & Brundin, P. (2013). Parkinson's Disease and Alpha Synuclein: Is Parkinson's Disease a Prion-Like Disorder?. Movement Disorders, 28(1), 31-40. (Year: 2013).*
International Search Report issued from corresponding PCT/NL2014/050671, dated May 28, 2015.
Calabro, Sara "5 Home Remidies for Constipation". Internet, Jun. 16, 2011 (Jun. 16, 2011). XP002726764. Retrieved from the Internet: URL:http://www.everydayhealth.com/digestive-health/five-home-remedies-for-constipation.aspx [retrieved on Jul. 7, 2014] paragraph [0004].
Leung, Lawrence et al., "Chronic constipation: an evidence-based review." Journal of the American Board of Family Medicine : JABFM Jul.-Aug. 2011, vol. 24. No. 4. Jul. 2011 (Jul. 2011). pp. 436-451, XP002726765, ISSN: 1557-2625 p. 437, left-hand column.
Luca. Gallelli, (2012). Constipation Treatment in Neurological Disorders, Constipation—Causes. Diagnosis and Treatment, Dr. Anthony CattoSmith (Ed.), ISBN: 978-953-51-0237-3, InTech, Available from: http://www.intechopen.com/books/constipationcauses-diagnosis-and-treatmenVconstipation-treatment-in-neurological-disorders.

(Continued)

*Primary Examiner* — Dale R Miller
(74) *Attorney, Agent, or Firm* — Banner & Witcoff, Ltd.

(57) ABSTRACT

The invention relates to a combination of a pyrimidine derivative and a fatty acid source for use in the treatment of constipation, in particular in the treatment of constipation in patients suffering from GI disorders, neurological disorders, or psychiatric disorders. Advantageously, the combination comprises one or more vitamins or fibres.

28 Claims, 5 Drawing Sheets

(56) References Cited

OTHER PUBLICATIONS

Park, Eun Sook, et al., "Colonic Transit Time and Constipation in Children With Spastic Cerebral Palsy," Arch Phys Med Rehabil vol. 85, Mar. 2004.
Wang Bo, et al., "Common Anorectal Disease Therapeutics," Scientific and Technical Documentation Press, Aug. 2013.

* cited by examiner

PYRIMIDINE DERIVATIVE AND A FATTY ACID SOURCE FOR USE IN THE TREATMENT OF CONSTIPATION

RELATED APPLICATION DATA

This application is a National Stage Application under 35 U.S.C. 371 of co-pending PCT application number PCT/NL2014/050671 designating the United States and filed Sep. 30, 2014; which claims the benefit of PCT application number PCT/NL2013/050879 and filed Dec. 6, 2013 each of which are hereby incorporated by reference in their entireties.

The invention relates to a combination of a pyrimidine derivative and a fatty acid source for use in the treatment of constipation, in particular in the treatment of constipation in patients suffering from GI disorders, neurological disorders, or psychiatric disorders.

The term GI-disorders covers a wide group of distinct disorders, varying from appendicitis, ileus, colitis, Crohn's disease, peptic ulcer, to anal fistulas, including enhanced or impaired motility of the gastro-intestinal tract (GIT) (too fast in diarrhoea, too slow in slow-transit constipation), and changes in the contractility of the rectal sphincter muscles (leading to faecal incontinence or faecal impaction/obstipation).

Constipation is a common cause of painful defecation. Severe constipation includes obstipation (failure to pass stools or gas) and faecal impaction, which can progress to bowel obstruction and become life-threatening.

Constipation is a symptom with many causes. These causes are of two types: obstructed defecation and slow transit (or hypomobility) in at least a part of the gastrointestinal tract. Known causes of slow transit constipation include diet, hormonal disorders such as hypothyroidism, side effects of medications, low-grade inflammation (also referred to as chronic inflammation), food allergies, and rarely heavy metal toxicity. Treatments include changes in dietary habits, laxatives, enemas, biofeedback, and in particular situations surgery may be required.

In general, compositions comprising nucleotides or fatty acids for use in the treatment of disorders of the gastro-intestinal tract (GI-disorders) are known in the art.

US 2007/0218112 relates to the use of glutamic acid or a nucleotide in relation to functional GI disorder. Various disorders are mentioned, including diarrhoea and constipation. A specific composition comprising nucleotide for use in the treatment of constipation is not mentioned. The examples focus on the role of glutamic acid in the gastro-intestinal tract.

US 2012/0189597A1 relates to a method of modifying cell energy charge, the method comprising administering to a mammal in need of same a nutritional composition comprising an effective amount of an exogenous nucleotide, e.g. in order to maintain gastrointestinal function in a mammal. Optionally, fish oil is present. The document is silent on treatment of constipation.

US2012/270830A1 relates to a nutritional composition comprising theanine and a nucleotide for treating a functional bowel disorder in a mammal. Optionally, the composition comprises fish oil. Various examples of bowel disorders are given, including dyspepsia, irritablebowel syndrome, functional faecal incontinence, functional anorectal pain and slow colonic transit. These disorders are distinct in nature, and some may even be considered as opposites (such as diarrhoea vs. slow transit). The document does not describe a combination of specifically a pyrimidine derivative and a polyunsaturated fatty acid for use in the treatment of constipation.

U.S. Pat. No. 5,709,888 B1 relates to a fatty acid mixture and to a mixture of the fatty acid mixture with nucleotides and/or nucleosides. The latter mixture is stated to be useful as an additive to milk for treating infants suffering from diarrhoea.

Thus, although a role of fatty acids and of nucleotides in the gastrointestinal system has been acknowledged in the art, it is not apparent from the cited prior art how to formulate a composition comprising a fatty acid source and a nucleic acid that is specifically useful in the treatment of constipation, let alone in the treatment of slow transit constipation.

It is an object of the present invention to provide a combination of specific components for use in the treatment of constipation, in particular for use in the treatment of slow transit constipation.

The terminology, slow transit constipation, was first coined in 1986 in a group of women who all displayed slow total gut transit time with a normal caliber colon in addition to a variety of other systemic symptoms (Preston Gut 1986).

It has now been found that a pyrimidine or derivative thereof in combination with a polyunsaturated fatty acid (PUFA) is effective in the treatment of constipation, in particular in that transit time through the gastro-intestinal tract is improved. The inventors found that a pyrimidine or derivative thereof in combination with a polyunsaturated fatty acid (PUFA) enhance transit through the whole length of the digestive tract (from stomach to rectum), greatly alleviating constipation.

In addition it was found that this combination of pyrimidine (derivative) and PUFA can significantly reduce formation of protein alpha-synuclein aggregates in the GIT (which can be detected in humans by biopsy of the sigmoid colon), possibly acting via TLR4.

TLR4, meant for Toll-like receptor 4, is a receptor binding to LPS (lipopolysaccharides) from GRAM negative bacteria, also present on neurones membranes, and is involved in the transport of alpha-synuclein into the cells.

Although not shown herein, there is experimental evidence that TLR4 KO mice subjected to the same rotenone treatment fail to show alpha-synuclein depositions and have a normal transit time, strongly indicating that TLR4 is required for the endocytosis of alpha-synuclein into the neurons of the myenteric plexus, and that this deposition accounts for the impairments in transit time.

This reduction of protein alpha-synuclein aggregates can potentially be used as a surrogate marker for neurodegenerative disease progression.

The inventors found that a composition comprising both the pyrimidine derivative and the polyunsaturated fatty acid (PUFA) was effective in reducing the transit time of stool through the intestinal system. In particular, the inventors found that the combination of pyrimidine derivative and the PUFA is useful in the treatment of slow transit constipation. This is evidenced by the Examples, in which a mouse model was used.

The invention is in particular considered useful for treatment of a human, preferably a human of at least 18 years of age, in particular a human of at least 50 years of age, more in particular an elderly human (at least 65 years of age).

It is further envisaged that in particular a human suffering from a neurological disorder benefits from treatment with a combination for use according to the invention.

Accordingly, the invention relates to a combination of a pyrimidine derivative and a polyunsaturated fatty acid having 18-24 carbon atoms for use in the prevention or treatment of constipation, preferably slow transit constipation.

The invention also relates to the use of a pyrimidine derivative and a polyunsaturated fatty acid having 18-24 carbon atoms for the manufacture of a medicament or of a combination for preventing or treating constipation, preferably slow transit constipation.

Preferably, the constipation is associated to a gastrointestinal disorder. In particular, said gastrointestinal disorder is a chronic inflammation of the mucosa of the gastrointestinal tract, preferably selected from the group consisting of ileus, colitis, inflammatory bowel disease, and peptic ulcer.

Alternatively, the constipation can be associated to a neurological disorder or a psychiatric disorder. The neurological disorder is preferably a peripheral neuropathy, an autonomic neuropathy, or an enteric nervous system neuropathy, preferably an autonomic neuropathy, or an enteric nervous system neuropathy.

Preferably, the neurological disorder is a progressive neurodegenerative disease.

Preferably, the neurological disorder is selected to from the group consisting of synucleopathies, diabetic neuropathy, Duchenne's dystrophy, cerebrovascular disease (more particularly stroke), Multiple Sclerosis, pure autonomic failure, and spinal cord injury, preferably selected to from the group consisting of cerebrovascular disease (more particularly stroke), Multiple Sclerosis, pure autonomic failure, spinal cord injury, and Parkinson's disease.

Preferably, the psychiatric disorder is a pervasive development disorder, preferably an austistic spectrum disorder.

Preferably, the psychiatric disorder is depression, in particular a depressive mood disorder.

In a specific embodiment, constipation is treated or prevented in a subject suffering from cerebral palsy.

According to a preferred embodiment, in a combination for use according to the invention, the polyunsaturated fatty acid is selected from the group of omega-3 polyunsaturated fatty acids, preferably provided as fish oil. More preferably, the omega-3 polyunsaturated fatty acids are selected from the group consisting of docosahexaenoic acid (DHA), docosapentaenoic acid (DPA), and eicosapentaenoic acid (EPA).

Preferably, the daily dosage of DHA administered via the combination is in the range of 300 mg to 4000 mg, more preferably in the range of 500 mg to 2500 mg.

Preferably, the daily dosage of DHA plus EPA administered via the combination is in the range of 400 mg to 5000 mg, more preferably in the range of 500 mg to 3000 mg, in particular in the range of 1000 mg to 3000 mg, more in particular in the range of 1000 mg to 2500 mg.

Preferably, a combination for use according to the invention comprises fish oil providing polyunsaturated fatty acid having 18-24 carbon atoms.

Preferably, in a combination for use according to the invention the pyrimidine derivative is a nucleobase, a nucleoside or a nucleotide; preferably is selected from the group of uridine, deoxyuridine, derivatised (deoxy)uridine, cytidine deoxycytidine and derivatised (deoxy)cytidines; more preferably is selected from the group of UMP, UDP, UTP, CMP, CDP, CTP dUMP, dUDP, dUTP, dCMP, dCDP and dCTP, wherein optionally one or more hydroxyl moieties of the (deoxy)ribose of said nucleotide is acylated.

In a particularly preferred embodiment, the nucleotide is UMP or acylated UMP.

In a particularly preferred embodiment, the nucleoside is uridine or acylated uridine, The acyl group may be any physiologically acceptable organic acid residue, in particular a C2-C24 organic acid residue. Preferred acylated forms of the pyrimidine sources are those wherein the (deoxy)ribose the has been acylated with acetic acid, n-caproic acid, caprylic acid, or n-capric acid, because these increase the bioavailability of the uridine source. Methods for reacting these medium chain fatty acids to uridines, for example to the 5' position of the uridine are known in the art per se for other fatty acids and comprise conventional acylation methods. In a further embodiment the uridine source is acylated with a PUFA, for instance an omega-3 PUFA.

A combination for use according to the invention can be administered as part of a nutritional composition. Preferably, a nutritional composition according to the invention comprises choline.

Preferably a nutritional composition according to the invention further comprises at least one of phospholipids, vitamin E, vitamin C, selenium, vitamin B12, vitamin B6 and folic acid; more preferably at least 2, 3, 4, 5, or 6 of phospholipids, vitamin E, vitamin C, selenium, vitamin B12, vitamin B6 and folic acid, even more preferably comprises phospholipids, vitamin E, vitamin C, selenium, vitamin B12, vitamin B6 and folic acid.

The invention further relates to a method for monitoring the treatment of constipation, preferably slow transit constipation, said method comprising administering a combination for use according to the invention, and measuring the level of alpha-synuclein aggregates in the colon.

The invention further relates to a method for monitoring the treatment of synucleopathies, preferably PD, dementia with Lewy bodies, or multiple system atrophy, more preferably for monitoring the treatment of PD, said method comprising administering a combination for use according to the invention, and measuring the level of alpha-synuclein aggregates in the colon.

Figure 4:
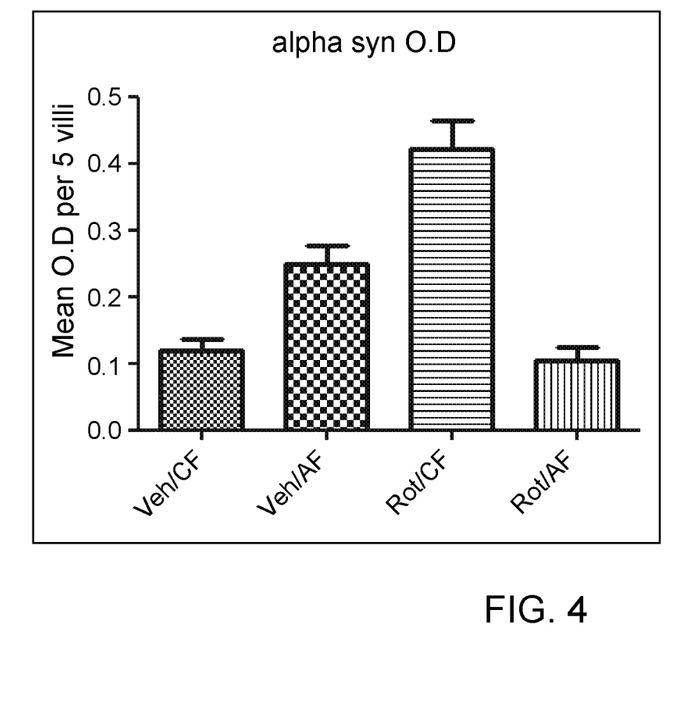
FIG. 4 shows results for Example 1: the intensity of immuno-histological staining of an antibody that detects alpha-synuclein in the colons of the four experimental groups of mice. Mean optical density (O.D.) is given of an area encompassing 5 villi.
Figure 5:
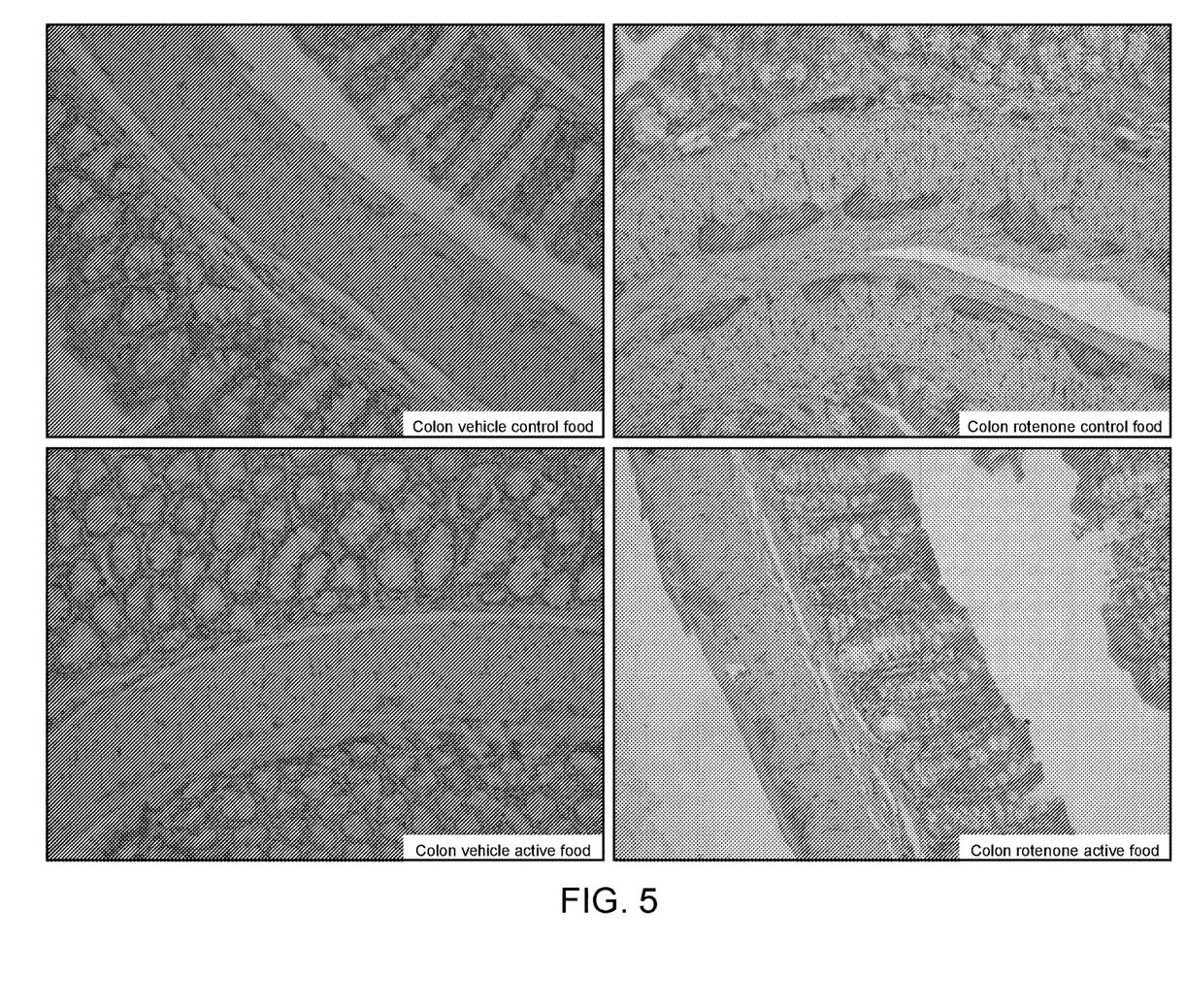
FIG. 5 shows Immuno-histological staining of an antibody (brown color) that detects alpha-synuclein in the colons of the experimental groups of mice (Example 1, Table 1).

E.g. from FIGS. 4 and 5, it can be inferred that the combination of UMP and a polyunsaturated fatty acid having 18-24 carbon attoms (as may be provided in the form of fish oil) can significantly reduce the formation of neurotoxic protein alpha-synuclein aggregates in the gastrointestinal tract. Wildtype mice treated with the pesticide rotenone have cytoplasmic alpha-synulcien depositions in the cells of the myenteric plexus of the intestinal wall which hinder intestinal movements. Treatment of these mice with the combination according to the invention reduced alpha-synuclein staining and improved transit time.

It was further found that use of a combination in accordance with the invention has a positive effect on motoric functioning in a mouse model for Parkinson Disease.

The term "a" or "an" as used herein is defined as "at least one" unless specified otherwise.

When referring to a noun (e.g. a compound, an additive etc.) in the singular, the plural is meant to be included.

The term "or" as used herein is to be understood as "and/or" unless specified otherwise.

For the purpose of clarity and a concise description features are described herein as part of the same or separate embodiments, however, it will be appreciated that the scope of the invention may include embodiments having combinations of all or some of the features described.

The term "constipation" refers in particular to its most used definition, i.e. for a human, evacuation of faeces that is less than normal, preferably less than three times a week.

The most widely used and accepted method of investigating constipated patients is the radio-opaque (solid markers) method (see for example Preston and Lennard-Jones, Gut, 1986, 27, 41-48)

The term 'fatty acid' is used herein in a way as is common in the prior art. Thus, the fatty acid may be provided as a free fatty acid or salt thereof or in a derivative form—suitable for use in a nutritional of pharmaceutical product—which is derivative form is degradable in the body to release the fatty acid. Suitable derivative forms include esters and ethers, including monoglyceride, diglyceride, triglyceride and phospholipid forms, as known in the art. In particular, good results have been achieved with a triglyceride.

When making calculations about amounts, one can assume the same bioavailability as the pure fatty acid and a contribution of fatty acid that is similar to the amount moles of fatty acids in the complete molecule, and correcting for the weight of the complete molecule.

Preferably, the combination for use according to the invention comprises at least one omega 3-PUFA, more preferably at least one PUFA selected from the group of docosahexaenoic acid (DHA), docosapentaenoic acid (DPA) and eicosapentaenoic acid (EPA).

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof.

More preferably, the combination for use according to the invention comprises at least DHA in triglyceride form.

Preferably, the combination for use according to the invention comprises DHA and EPA in sufficient amount for the administration of 400 to 5000 mg (DHA+EPA) per day, more preferably 500 to 3000 mg per day, most preferably 1000 to 2500 mg per day.

The proportion of (DHA+EPA) of the total fatty acids present in the combination for use according to the invention is preferably 5-50 wt. %, more preferably 10-45 wt. %, most preferably 15-40 wt. %.

More preferably, the present combination for use according to the invention comprises DHA in sufficient amount for the administration of DHA in an amount of 300 to 4000 mg per day, more preferably 500-2500 mg per day.

The present combination for use according to the invention preferably contains a very low amount of arachidonic acid (AA).

The present combination for use according to the invention preferably comprises less than 5 wt. % arachidonic acid based on total fatty acids, more preferably below 2.5 wt. %, e.g. down to 0.5 wt %.

Preferably the weight ratio DHA/AA in the present combination for use according to the invention is at least 5, preferably at least 10, more preferably at least 15, preferably up to e.g. 30 or even up to 60.

The ratio omega-6/omega-3 fatty acids in the present combination for use according to the invention is preferably below 0.5, more preferably below 0.2, e.g. down to 0.05 or to 0.01. In particular, the ratio omega-6/omega-3 fatty acids (C 20 and higher) in the present combination for use according to the invention is preferably below 0.3, more preferably below 0.15, e.g. down to 0.06 or to 0.03.

The present combination for use according to the invention preferably comprises 1-40 wt. % DHA based on total fatty acids, preferably 3-36 wt. % DHA based on total fatty acids, more preferably 10-30 wt. % DHA based on total fatty acids.

The present combination for use according to the invention preferably comprises 0.5-20 wt. % EPA based on total fatty acids, preferably 2-10 wt. % EPA based on total fatty acids, more preferably 5-10 wt. % EPA based on total fatty acids.

The daily dosage of polyunsaturated fatty acid having 18-24 carbon atoms administered via the combination usually is in the range of 0.4-15 grams, preferably in the range of 0.6-10 g, in particular in the range of 1-5 g.

In particular, good results have been achieved with a combination comprising both EPA and DHA. If both are present, the weight to weight ratio EPA:DHA usually is in the range of 1:99 to 99:1, preferably in the range of 1:10-5:1, in particular in the range of 1:5-1:2.

If EPA and/or DHA are present, the total daily dosage of DHA plus EPA taken together preferably is in in the range of 300-5000 mg/day, preferably in the range of 500-3000 mg/day, in particular in the range of 1000-2500 mg/day In an advantageous embodiment, fish oil or algae oil is suitable as a source of PUFA. A fish oil is particularly suitable as a source for the PUFA.

The term 'pyrimidine derivative' is used herein for molecules having a heterocyclic six membered ring, the ring containing a nitrogen at the 1 and the 3 position, and a carbon at the 2, 4, 5 and 6 position, wherein at least of the carbons is provided with a functional group, in particular a functional group selected from the group of keto-groups (=O) and primary amine groups (—NH$_2$). The heterocyclic ring usually comprises one or two double bonds. Preferably, at least one of the nitrogens in the ring is bound to a sugar group, in particular a ribose or deoxyribose.

Preferably, the pyrimidine derivative is selected from the group of pyrimidine nucleobases and derivatives thereof, in particular from the group of uracil, cytosine, and derivatives thereof. Preferred derivatives thereof are nucleosides of uracil or cytosine and nucleotides of uracil or cytosine. Thus, in a preferred embodiment, the combination provides at least one nucleotide selected from the group of UMP, UDP, UTP, CMP, CDP, CTP dUMP, dUDP, dUTP, dCMP, dCDP and dCTP.

The nucleoside or nucleotide may be used as such, or one or more of its functional groups may be derivatised. In particular an amino group attached to the heterocyclic six membered ring may be derivatised or one or more of the hydroxyl groups of the ribose or deoxyribose of the nucleoside or nucleotide may derivatised, preferably esterified (acylated), for instance with a C1-C24 carboxylic acid.

In an embodiment, the pyrimidine derivative comprises a fatty acid moiety selected from the group of PUFA's. Thus, in a specific embodiment, the combination for use of the invention comprises the PUFA and the pyrimidine derivative combined in a single molecule, which may be hydrolysed in vivo. Esters of a pyrimidine derivatives and methods for making those are generally known in the art. Such derivatives have amongst others been described in EP 1,390,378 and in U.S. Pat. No. 5,470,838.

Preferably, the combination for use according to the invention comprises a source of uridine selected from uridine, deoxyuridine, uridine phosphates, uracil, acylated uridine, and cytidine.

Dietary cytidine, being converted into uridine in humans, can be regarded as a source of uridine in the context of the present invention. Therefore, the combination for use according to the invention can comprise, as a source of uridine, cytidine, deoxycytidine, cytidine phosphates, cytosine and/or acylated cytidine.

Preferably, the present combination for use according to the invention comprises uridine and/or uridine phosphate, more preferably comprises uridine phosphate.

In particular, the present combination for use according to the invention comprises one or more uridine phosphates selected from uridine monophosphate (UMP), uridine diphosphate (UDP) and uridine triphosphate (UTP), and more preferably UMP.

Most preferably the present combination for use according to the invention comprises UMP and/or uridine. Preferably at least 50 wt. % of the uridine in the present combination for use according to the invention is provided by UMP, more preferably at least 75 wt. %, most preferably at least 95 wt. %.

The present combination for use according to the invention is preferably administered (or is in a format) to provide uridine (the cumulative amount of uridine, deoxyuridine, uridine phosphates, uracil and acylated uridine derivatives) in an amount of 0.08-3 g per day, preferably 0.1-2 g per day, more preferably 0.2-1 g per day.

The present combination for use according to the invention preferably comprises uridine in an amount of 0.08-3 g UMP per 100 ml of a liquid product, preferably 0.1-2 g UMP per 100 ml of a liquid product, more preferably 0.2-1 g per 100 ml liquid product.

Preferably 1-37.5 mg UMP per kilogram body weight is administered per day.

The required dosages of the equivalents on a weight base can be calculated from the dose for UMP by taking equimolar amounts using the molecular weight of the equivalent and of UMP, the latter being (about) 324 Dalton. Thus, a daily dosage of the pyrimidine advantageously is in the range of 3-116 µmol per kg body weight per day.

The combination is preferably administered at least once per day, in particular 2-10 times per day. For embodiments wherein the combination or composition is administered less than once a day, the unit dosages (dosage per serving) of the active ingredients is usually within the range for the daily dosages mentioned elsewhere herein, although the concentration of the active ingredients may be higher.

In an advantageous embodiment, the combination is administered as part of a nutritional composition. The nutritional composition usually further comprises a digestible carbohydrate fraction and/or a proteinaceous matter fraction.

Further, the composition may comprise a lipid fraction comprising the PUFA and one or more other lipids.

In a specific embodiment, the nutritional composition comprises dietary fibre. The presence of fibre in combination with the PUFA and the pyrimidine has been found to have a positive effect on constipation, in particular slow transit constipation. Moreover, it has been found to provide an improvement in motoric functioning in a subject suffering from a progressive neurodegenerative disorder, such as Parkinson's disease.

The total daily dosage of fibre in accordance with the invention preferably is 1 to 15 g, more preferably of 3 to 12 g, in particular 4-10 g. In terms of total fibre content in a product for use in accordance with the invention the content of the fibre preferably is 1-15 g/100 g, in particular 3-10 g/100 g product.

The fibres may be selected from soluble fibres and insoluble fibres.

The fibres are generally composed of a plurality of carbohydrate units. The fibres may be short-chain indigestible carbohydrates or long-chain indigestible carbohydrates. Dependent on the type of fibre, national food regulations may have different definitions for what constitute short chain or long chain. As used herein, short chain fibres generally have a polymerization degree of less than 20, in particular of 2-12 less, more in particular 3-9; long chain fibres have a polymerization degree at least one higher than specified for short chain fibres, so 10 or more, 13 or more or 20 or more.

The inventors surprisingly found that the presence of a specific group of fibres in combination with an omega-3-PUFA (EPA/DHA) and a pyrimidine derivative (a uridine source) has a positive effect on consitpation. As illustrated by the Examples, mice treated with a diet containing butyrate producing fibre performed better with respect to colon length and intestinal transit than mice treated with a diet without such fibre. From the Examples, the inventors realise that in particular Parkinson patients may benefit from the butyrate producing fibre in combination with a uridine source, omega3-PUFA and optionally one or more other components, such as vitamin D.

Butyrate producing fibres are indigestible carbohydrates that have butyrate as a breakdown product when fermented by colonic flora. The term 'butyrate producing fibre' is used herein in particular for fibre that is capable of producing at least 0.5 mmol or more, preferably at least 0.75 mmol or more, more preferably at least 1.0 mmol or more butyrate/gram fibre after 24 hours of in vitro fermentation. In practice, the maximum amount of butyrate producible under these condititions is usually 5 mmol or less, in particular 3.5 mmol or less, more in particular 2.5 mmol or less butyrate/gram fibre after 24 hours of in vitro fermentation.

The producible amount of butyrate is determinable using a semi-dynamic colon model (e.g. using a TIM artificial gut system). In an alternative model, fresh faecal samples are collected from healthy adults (without gastro-intestinal problems; no use of antibiotics for a last 2 weeks prior to sample taking). Faecal samples are divided in smaller portions and mixed with glycerol (10%) in an anaerobic cabinet and stored at −80° C. In each experiment the faecal samples from all donors are pooled at equal concentrations and mixed together in an anaerobic cabinet, to avoid subject-dependent variation in the adult microbiota as much as possible. The samples are inoculated with a fibre under fermentation conditions and fermentation is allowed to take place. Butyrate production is determined after 24 hrs using GC. In particular the model makes use of samples from four healthy adults (e.g., three male donors and one female donor) in the age of 19-35 years;

the fibre is inoculated in a faeces suspension at a content of 200 mg/6 ml faeces suspension the faeces suspension is made by mixing aeces with a fermentation medium as 1:5 v/v;

the fermentation medium: buffered peptone water 3.0 g/l, Yeast Extract 2.5 g/l, Tryptone 3.0 g/l, L-Cysteine-HCl 0.4 g/l, Bile salts 0.05 g/l, K2HPO4.3H2O 2.6 g/l, NaHCO3 0.2 g/l, NaCl 4.5 g/l, MgSO4.7H2O 0.5 g/l, CaCl2. 2H2O 0.3 g/l, FeSO4.7H2O 0.005 g/l. Ingredients can be added one by one in 800 ml water, pH is adjusted to 6.3±0.1 with K2HPO4 or NaHCO3 and volume is filled up to 1 liter. Medium is sterilized for 15 minutes at 121° C.

The fermentation temperature is 37° C.

The total dosage of butyrate producing fibre in accordance with the invention preferably is 1 to 15 g per dosage, more preferably of 2 to 10 g per dosage, in particular 3-8 g per dosage. The total butyrate producing fibre content, based on total fibre content in a composition for use in accordance with the invention is up to 100 wt %, in particular 99 wt. % or less, more in particular 95 wt. % or less. The total butyrate producing fibre content, based on total fibre content preferably is at least 50 wt. %, based on total fibre content, preferably at least 70 wt. %, more preferably at least 80 wt. %, in particular 90 wt. % or more.

Preferably the combination or nutritional composition for use according to the invention comprises fibre in an amount sufficient to produce 0.3-5 mmol, more preferably 0.5-3.5, in particular 0.7-3, more in particular 1.0-2.5 mmol butyrate per gram fibre, under the using a semi-dynamic colon model, described above.

Preferred soluble butyrate producing fibres include fructooligosaccharides (FOS), galactooligosaccharides (GOS), bran and dextrins (e.g. Nutriose®). These are well soluble and are a suitable substrate for colonic flora to produce butyrate, when fermented. Preferred brans are oat bran, rice bran and wheat bran. In a particularly preferred embodiment, several butyrate producing fibres are used, such as at FOS and a dextrin plus optionally bran and/or GOS; or FOS and bran plus optionally dextrin and/or GOS. Good results have been achieved with a combination of short chain FOS, long chain FOS, oat bran, GOS and dextrin. In an other preferred embodiment, the combination is part of a nutritional composition that comprises one or more butyrate producing fibres but that is essentially free of GOS. Such composition preferably is a milk-free composition.

Preferred insoluble butyrate producing fibres include resistant starch, such as high-amylose starch or retrograded or RS3 starch. Resistant starch is suitable to provide a particularly high butyrate production per g of resistant starch.

Resistant starch is defined to be as those starches which remain intact after digestion during 2 hours in the system of Englyst et al Am J Clin Nutr 1999, 69, 448-454. Commercially available resistant starches are Actistar and Novelose 330.

Preferred resistant starches are resistant starches from rice or corn.

In a specific embodiment, the resistant starch comprises more than 50 wt % linear polymers of alpha 1,4 glucans which have a degree of polymerization between 10 and 35. Suitable sources of such resistant starches are beans, peas, heat-treated potatoes and heat-treated cereals. Simultaneous presence in the colon of resistant starch and beta glucans, in combination with a xylan will support of growth of the right type of butyrate generating bacteria species.

In a specific embodiment, the nutritional composition comprises one or more free amino acids or salts thereof.

In a specific embodiment, the nutritional composition comprises one or more trace elements.

In a specific embodiment, the nutritional composition comprises one or more vitamins.

In a specific embodiment, the composition contains choline. Preferably the present nutritional composition contains choline and/or phosphatidylcholine. Preferably the nutritional composition is administered (or is in a format) for providing more than 50 mg choline per day, preferably 80-2000 mg choline per day, more preferably 120-1000 mg choline per day, most preferably 150-600 mg choline per day.

Preferably the present nutritional composition contains 50 mg to 3 gram choline per 100 ml of a liquid formula, preferably 200 mg-1000 mg choline/100 ml.

The present nutritional composition may advantageously contain phospholipids, preferably provided in the form of lecithin The present nutritional composition is preferably a liquid composition, wherein lecithin is provided in an amount of 0.01 and 1 gram lecithin per 100 ml, more preferably between 0.05 and 0.5 gram lecithin per 100 ml.

The present nutritional composition may advantageously contain vitamins, preferably vitamin C, vitamin E and B vitamins, more preferably vitamin C, vitamin E, vitamin B6, vitamin B12 and folic acid.

Advantageously, vitamin B12 and folate are included.

The present nutritional composition preferably comprises 50 to 1000 µg folic acid, more preferably 150 to 750 µg, most preferably 200 to 500 µg folic acid, per 100 ml liquid product.

The present method preferably comprises the administration of 50-1000 µg folic acid per day, more preferably 150-750 µg, most preferably 200-500 µg folic acid per day.

The present nutritional composition preferably comprises 0.5 to 15 µg vitamin B12, more preferably 1 to 10 µg, most preferably 1.5 to 5 µg vitamin B12, per 100 ml liquid product.

The present method preferably comprises the administration 0.5-15 µg vitamin B12 per day, more preferably 1-10 µg, most preferably 1.5-5 µg vitamin B12 per day.

Advantageously, the present nutritional composition according to the invention comprises 0.5 to 3 mg, preferably 0.5-2 mg vitamin B6, per 100 ml liquid product.

Preferably, vitamin B6, vitamin B12 and folate are included.

Further, the inventors found a positive effect of vitamin D in a combination of the invention. Vitamin D is in particularly suitable to be included in a combination of the invention for an elderly person, a Parkinson patient or a dementia patient, e.g. an Alzheimer patient.

Good results have been obtained with a composition comprising vitamin D3 (cholecalciferol, calcifediol, calcitriol).

If present, the concentration of vitamin D, preferably of vitamin D3, in a nutritional composition for use in accordance with the invention usually is in the range of 5-110 µg/100, in particular in the range of 6-85 µg/100 g preferably in the range of 10-50 µg/100 g, more preferably 15-45 µg/100 g.

The combination for use according to the invention usually provides vitamin D to the mammal, in particular human, that is treated in a in a daily dosage of up to about 50 µg. If present, the daily dosage preferably is at least 5 µg, more preferably 25-40 µg. For a liquid product, the vitamin D3 content preferably is 5-85 µg per unit dosage. The unit dosage of a liquid product preferably has a volume of 50-250 ml, in particular 100-150 ml.

The nutritional composition may be a fluid drinkable composition, a spoonable composition or a solid composition. Preferably, the nutritional composition is a liquid composition, preferably liquid ready to drink composition.

The combination or nutritional composition according to the invention, is preferably administered to the subject in need thereof by oral ingestion. In an alternative embodiment, tube feeding is used.

In yet another embodiment, the combination is administered rectally.

A combination for use according to the invention, or a nutritional composition of the invention, including any embodiment described therein, is preferably for preventing or treating constipation, in particular slow transit constipation (also referred to as slowed transit constipation), in a subject suffering from, or at risk of suffering from a neurological disorder. As used herein 'at risk' means in particular a significantly above average risk.

It is acknowledged as a general experience that constipation is frequent in acute admitted stroke patients. One possible reason could be an impaired coordination of the peristaltic wave and the relaxation of the pelvic floor and external sphincter.

Gastrointestinal dysfunctions is frequent and sometimes a dominant symptom of Parkinson's disease (PD), where constipation could result from a decreased bowel movement frequency. It has been reported that more than 50% of PD patients suffer from moderate to severe constipation. Some of these PD patients had pathologically prolonged colon transit time, in other words suffer from slow transit constipation. The reduction of the alpha-synuclein aggregates in the colon might favour a better functioning of the autonomic nervous system (ANS) and/or the enteric nervous system (ENS), and therefore allow a better functioning of the peristalsis of the gastrointestinal tract, and more generally a better functioning of the digestive process (meant to encompass ingestion, digestion, absorption of the nutrients and defecation).

Moreover, it has been shown that anticholinergic agents, and Levo-dopa (l-dopa), by slowing down the bowel movements, enhance the constipation problem.

It has been shown that slow-transit and gastroparesis causes the degradation of l-dopa into dopamine in the intestinal tract. Dopamine in turn inhibits cholinergic fibers and execerbates respectively the problems of slow transit and delayed gastric emptying even further.

Studies have shown that the l-dopa is more effective when the constipation problem is addressed simultaneously.

Therefore, a combination for use according to the invention, or a nutritional composition of the invention can be used in parallel (i.e. administered simultaneously, or before, or after) to the use of an anticholinergic agent for treating PD, such as benzhexol, orphenadrine, benztropine, bornaprine, benapryzine, or mithixine, or to the use of 1-dopa.

A combination for use according to the invention, or a nutritional composition of the invention can be used for treating synucleopathies related/associated constipation, including (besides PD) dementia with Lewy bodies, and multiple system atrophy.

Bowel dysfunctions in patients with multiple sclerosis is common. Possibly through the attenuation of chronic (low grade) inflammation, attenuation possibly obtained by down regulating TLR4, a combination for use according to the invention, or a nutritional composition of the invention is expected to improve the constipation issues, in particular the slow transit constipation.

It is well documented that patients having spinal cord injury suffer from prolonged colonic transit time, resulting in slow transit constipation. Possibly through the better functioning of the autonomic nervous system (ANS) and/or the enteric nervous system (ENS), a combination for use according to the invention, or a nutritional composition of the invention is expected to improve the constipation issues, in particular the slow transit constipation.

There are other diseases affecting the peripheral nervous system and/or motor neurones to which constipation is associated. Examples of such diseases are diabetic neuropathy, pure autonomic failure (PAF).

Possibly through the better functioning of the autonomic nervous system (ANS) and/or the enteric nervous system (ENS), a combination for use according to the invention, or a nutritional composition of the invention is expected to improve the constipation issues, in particular the slow transit constipation. (See Winge et al., 2003, J Neurol Neurosurg Psychiatry; 74; 13-19)

Possibly through the attenuation of chronic (low grade) inflammation, attenuation possibly obtained by down regulating TLR4, a combination for use according to the invention, or a nutritional composition of the invention is expected to improve the constipation issues, in particular the slow transit constipation, in patients suffering from GI-disorders, such as ileus, colitis, inflammatory bowel disease (more particularly Crohn's disease or ulcerative colitis), and peptic ulcer.

The GI-disorders triggering chronic inflammation of the mucosa of the gastrointestinal tract enhance the disruption of the mucosal integrity, which activate TLR4.

Possibly through the attenuation of chronic (low grade) inflammation, attenuation possibly obtained by down regulating TLR4, a combination for use according to the invention, or a nutritional composition of the invention is expected to improve the constipation issues, in particular the slow transit constipation, in patients suffering from PDD (pervasive development disorder), in particular ASD (autism spectrum disorder).

The invention will now be illustrated by the following examples.

EXAMPLE 1

Figure 1:
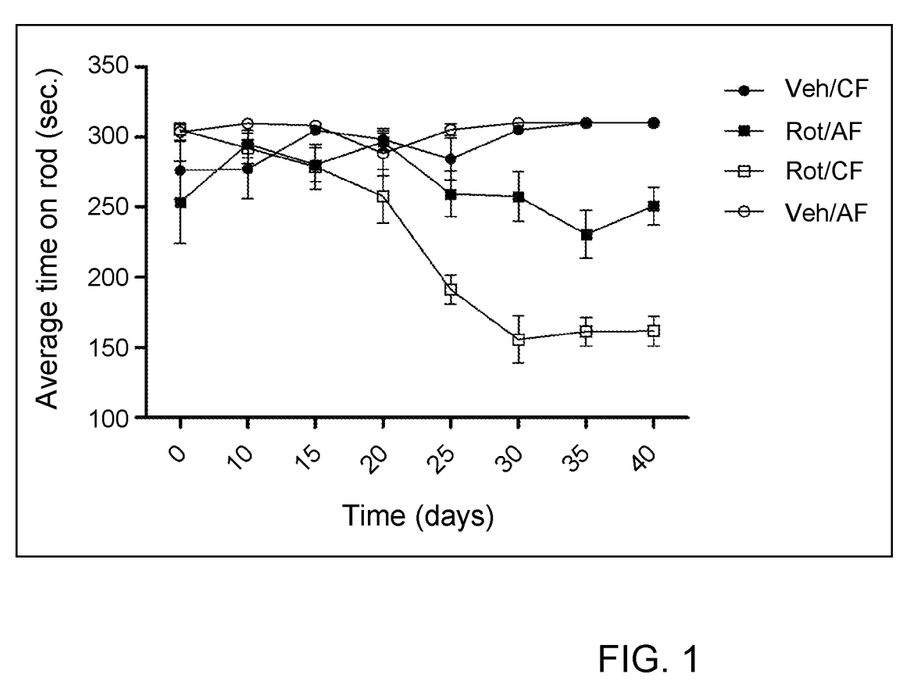
FIG. 1 shows results for Example 1: the average time on rotarod (in seconds) at different times (in days) after intrastriatal injection with vehicle (Veh) or rotenone (Rot). Four groups of mice are shown as explained in Table 1.

Constipation, the most important and debilitating non-motor symptom of Parkinson's disease (PD), was induced in mice by intra-striatal injection of 2.7 µg of rotenone by stereotaxic surgery into the brain. Epidemiological studies had previously shown that exposure to this pesticide induced Parkinson's disease (PD). In addition to the observed constipation, the intra-striatal injection with rotenone also resulted in the well-known motor symptoms of PD, shown by the impaired ability of the mice to remain on a moving rotarod (see FIG. 1). The rotarod treadmill consists of a plastic rod, with a non-slippery surface, above the base (trip plate). Mice were placed on an accelerating rod with speeds starting with 2 rpm and gradually increasing to 20 rpm. The rodent's ability to remain on the rotating rod (time to first fall) was recorded for a maximum of 5 minutes. Before baseline, mice were trained with the rotarod apparatus to rule out learning effects throughout the experiment.

In this animal model, dietary intervention with UMP+fish oil was shown to normalize intestinal transit time to control levels and to treat constipation.

Four experimental groups of 10 mice each were used which were either injected with rotenone or vehicle and which received control or active diet (=UMP+fish oil) according to Table 1. The specific composition of the control and active diets are presented in Table 2. Dietary intervention was started one week before surgery and was continued for six weeks.

TABLE 1

Experimental groups

| Group | Intra-striatal injection | Diet |
|---|---|---|
| Veh/CF | Vehicle | Control |
| Veh/AF | Vehicle | UMP + fish oil |
| Rot/CF | rotenone | Control |
| Rot/AF | rotenone | UMP + fish oil |

TABLE 2

Composition of the diets

| | animal food based on AIN -93 M Reeves, et al. (1993) | |
|---|---|---|
| | g/100 g diet Control | g/100 g diet Fish + UMP |
| Corn starch | 31.10 | 29.30 |
| Casein (>85% protein) | 14.00 | 14.00 |
| corn dextrine | 15.50 | 15.50 |
| Sucrose | 10.00 | 10.00 |
| Dextrose | 10.00 | 10.00 |
| Fibers | 5.00 | 5.00 |
| Minerals mix (AIN-93M-MX) (*) | 3.50 | 3.50 |
| Vitamins mix (AIN-93-VX) (*) | 1.00 | 1.00 |
| Fat | 4.77 | 4.77 |
| saturated fat | 1.3 | 1.2 |
| Monounsaturated fatty acids (MUFA) | 1.100 | 1.100 |
| PUFA | 2.300 | 2.200 |
| EPA (C-20:5w3) | 0.000 | 0.300 |
| DHA (C-22:6w3) | 0.000 | 0.700 |
| Additions: | | |
| L-cystine | 0.180 | 0.180 |
| Choline bitartrate (41.1% choline) | 0.250 | 0.250 |
| Tert-butylhydroquinone | 0.0008 | 0.0008 |
| UMP disodium (24% H2O) | 0 | 1.0 |
| Total | 100.0 | 100.0 |
| Energy | 344.6 | 345.5 |

(*) See Reeves 1993 - JNutr; Nov; 123(11); 1939-51.

Figure 2:
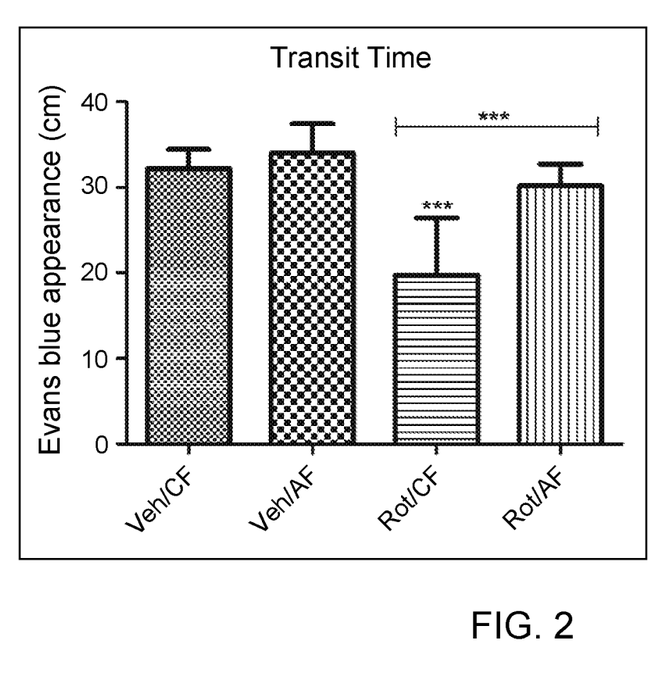
FIG. 2 shows results for Example 1: Length of blue colored intestines upon administration of 2.5% Evans Blue solution intra gastrically one hour before sacrifice. Average lengths and standard errors are given four each experimental group (Table 1).

UMP+fish oil significantly increased the transit speed of gastrically applied Evans Blue through the small intestine of rotenone injected mice (see FIG. 2). For this purpose, 2.5% Evans Blue dye in 1.5% methylcellulose solution (0.3 ml per animal) was administered intra-gastrically through a stainless steel cannula an hour before sacrificing the mice, six weeks after surgery. The length of blue-colored intestines (in cm) was taken as a measure of intestinal transit time (shown in FIG. 2).

Figure 3:
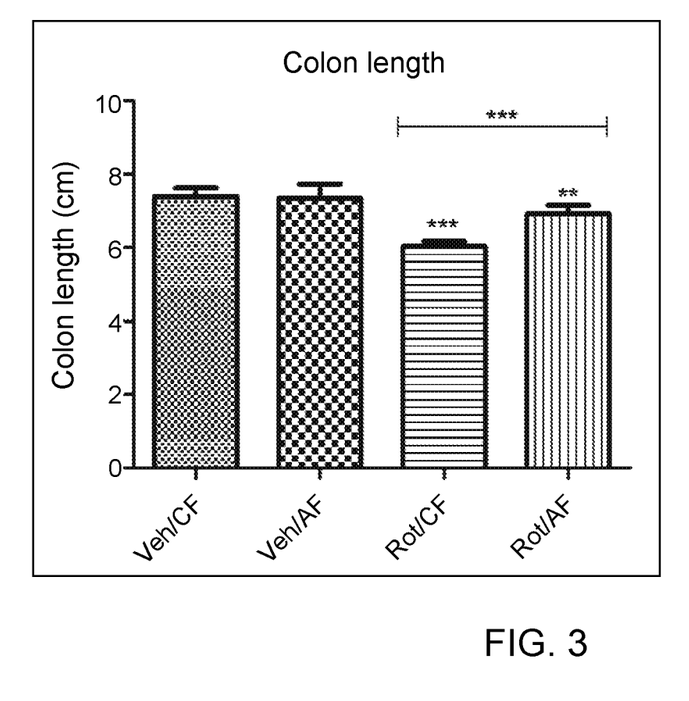
FIG. 3 shows results for Example 1: average lengths of colons (in cm) in the four experimental groups (Table 1).

The length of the colons of the rotenone-injected mice on UMP+fish oil diet, measured six weeks after surgery, also restored almost back to normal (see FIG. 3).

Furthermore, the GI tract of the rotenone-injected mice that were given UMP+fish oil had significantly less of the characteristic alpha-synuclein protein aggregates than the rotenone-injected mice on control diet (see FIG. 4 and FIG. 5). The presence of alpha-synuclein aggregates in the sigmoid colon of Parkinson patients may be used as surrogate marker for the disease.

EXAMPLE 2

Ready to use liquid product providing per 100 mL:
Energy: 50-120 kcal
Protein: 0-10 g
Lipids: 1-5 g
Digestible carbohydrates: 4-30 g
and which comprises:
DHA+EPA+DPA=1000-2000 mg
Uridine monophosphate (disodium salt) 0.5 g

EXAMPLE 3

A preferred nutritional composition according to the invention comprises, per daily dose or per 100 ml composition:
100-500 mg, preferably 200-400 mg EPA,
900-1500 mg, preferably 950-1300 mg DHA
50-600 mg, preferably 60-200 mg phospholipids,
200-600 mg, preferably 300-500 mg choline,
400-800 mg, preferably 500-700 mg UMP,
20-60 mg, preferably 30-50 mg vitamin E (alpha-TE),
60-100 mg, preferably 60-90 mg vitamin C,
40-80 µg, preferably 45-65 ug selenium,
1-5 µg, preferably 2-4 µg vitamin B12,
0.5-3 mg, preferably 0.5-2 mg vitamin B6, and
200-600 µg, preferably 300-500 µg folic acid.

EXAMPLE 4

Liquid ready to use product as in Example 2 or 3 for diabetic patient suffering from neuropathy, in which the carbohydrate fraction is composed of (per 100 mL):
1.5 g galactose
3 g palatinose
1 g slowly digestible starch
0.2 g fructose
3 g maltodextrins
2 g glucose
1.05 g isomalto oligosaccharides

EXAMPLE 5

The effects of a diet comprising a pyrimidine derivative (UMP) and a PUFA source (DHA) in a therapeutic setting were studied, wherein treatment with a diet according to the invention was initiated 4 weeks after injection with 5.4 µg rotenone or a vehicle and continued for seven weeks. Six experimental groups of male C57B1/6J mice were used which were either treated with vehicle (Sham) or rotenone and which either received a control diet or a diet according to the invention (diet 1 or diet 2), as indicated in the following table:

TABLE 3

Experimental groups

| Group | Intra-striatal injection | diet |
|---|---|---|
| Sham + Control Food (control) | Sham | Control |
| Sham + Diet 1 (control) | Sham | Uridine source + DHA |
| Sham + Diet 2 (control) | Sham | Uridine source + DHA + butyrate producing fibres |

TABLE 3-continued

Experimental groups

| Group | Intra-striatal injection | diet |
|---|---|---|
| Rotenone + Control Food | Rotenone | Control |
| Rotenone + Diet 1 | Rotenone | Uridine source + DHA |
| Rotenone + Diet 2) | Rotenone | Uridine source + DHA + butyrate producing fibres |

The compositions of the control and active diets are presented in the following Table.

TABLE 4

Composition of the diets

| | animal food based on AIN -93 M Reeves, et al. (1993) | | |
|---|---|---|---|
| | g/100 g diet Control | g/100 g diet Diet 1: Fish oil + UMP | g/100 g diet Diet 2: Fish oil + Uridine + buty-- rate producing fibers |
| Corn starch | 31.10 | 29.30 | 31.97 |
| Casein (>85% protein) | 14.00 | 14.00 | 14.00 |
| corn dextrine | 15.50 | 15.50 | 14.20 |
| Sucrose | 10.00 | 10.00 | 10.00 |
| Dextrose | 10.00 | 10.00 | 10.00 |
| Fibers (cellulose) | 5.00 | 5.00 | 0 |
| Butyrate producing fibers | 0 | 0 | 7.27[1] |
| Minerals mix (AIN-93M-MX) (*) | 3.50 | 3.50 | 3.50 |
| Vitamins mix (AIN-93-VX) (*) | 1.00 | 1.00 | 1.00 |
| Fat | 4.77 | 4.77 | 4.77 |
| saturated fat | 1.3 | 1.2 | 1.2 |
| Monounsaturated fatty acids (MUFA) | 1.1 | 1.1 | 1.1 |
| PUFA | 2.3 | 2.2 | 2.2 |
| EPA (C-20:5w3) | 0.0 | 0.3 | 0.5 |
| DHA (C-22:6w3) | 0.0 | 0.7 | 0.7 |
| Additions: | | | |
| L-cystine | 0.180 | 0.180 | 0.180 |
| Choline bitartrate (41.1% choline) | 0.250 | 0.250 | 0.922 |
| Tert-butylhydroquinone | 0.0008 | 0.0008 | 0.0008 |
| Additional vitamins[2] | | | 0.688 |
| Soy lecithin | | | 0.755 |
| UMP disodium (24% H2O) | 0 | 1.0 | |
| Uridine (pure) | | | 0.511 |
| Total | 100.0 | 100.0 | 100.0 |
| Energy | 344.6 | 345.5 | 358.0 |

[1]Butyrate producing fibres (5 gram per 100 g diet):
1.50 g GOS
0.17 g long-chain FOS
1.67 g short- chain FOS
1.67 g nutriose
And further 0.5 g lactose and 0.5 g the carbohydrate and moisture to 7.27 g
[2]Additional vitamins (per 100 g diet)

| | |
|---|---|
| Ascorbic acid (100% pure) | 0.16 g |
| Vit. E (Tocopherol acetate, 50%) | 0.465 g |
| Vitamine D (cholecalciferol, 500.000 IU/g) | 5.6 µg |
| Vit. B6 (Pyridoxin hydrochloride, 82%) | 0.00407 g |
| Folic acid (100%) | 0.00060 g |
| Vit. B12 (Cyanocobalamin 0.1%) | 0.0575 g |
| Na selenite•5 H2O | 0.00034 g |

Diet 1 was composed of the control diet plus additionally UMP and DHA (fish oil).

Diet 2 was as Diet 1, without cellulose, but instead additionally a mixture of galactooligosaccharides and fructooligosaccharides (both long chain and short chain fructooligosaccharides and instead of UMP uridine).

Figure 6:
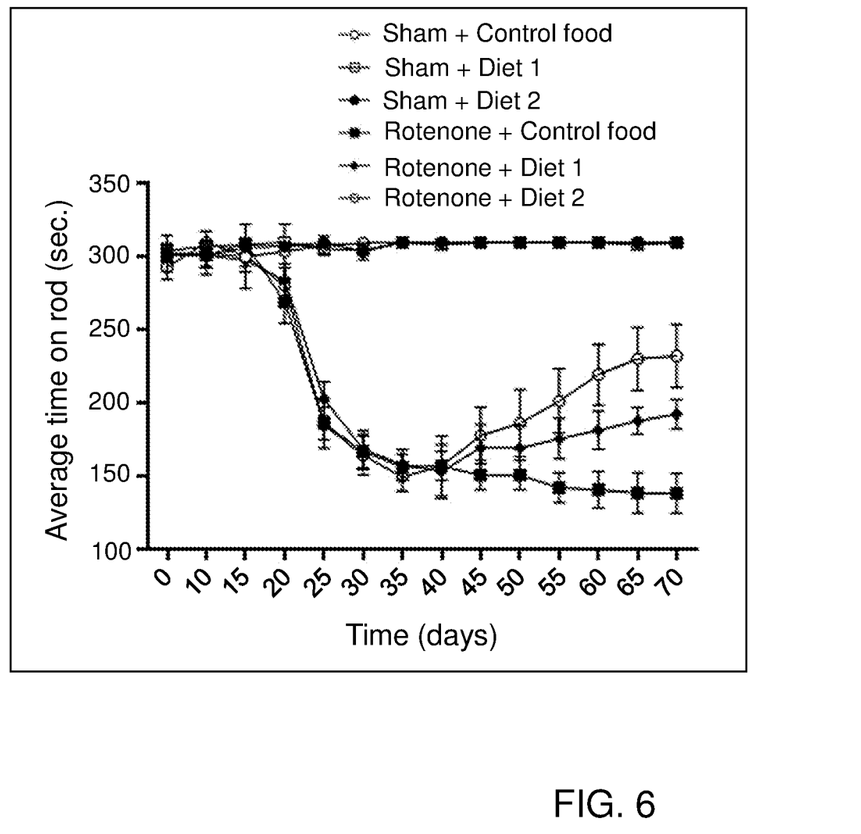
FIG. 6 shows results for Example 5, regarding the time spent by mice on a Rotarod in a therapeutic setting.
Figure 7:
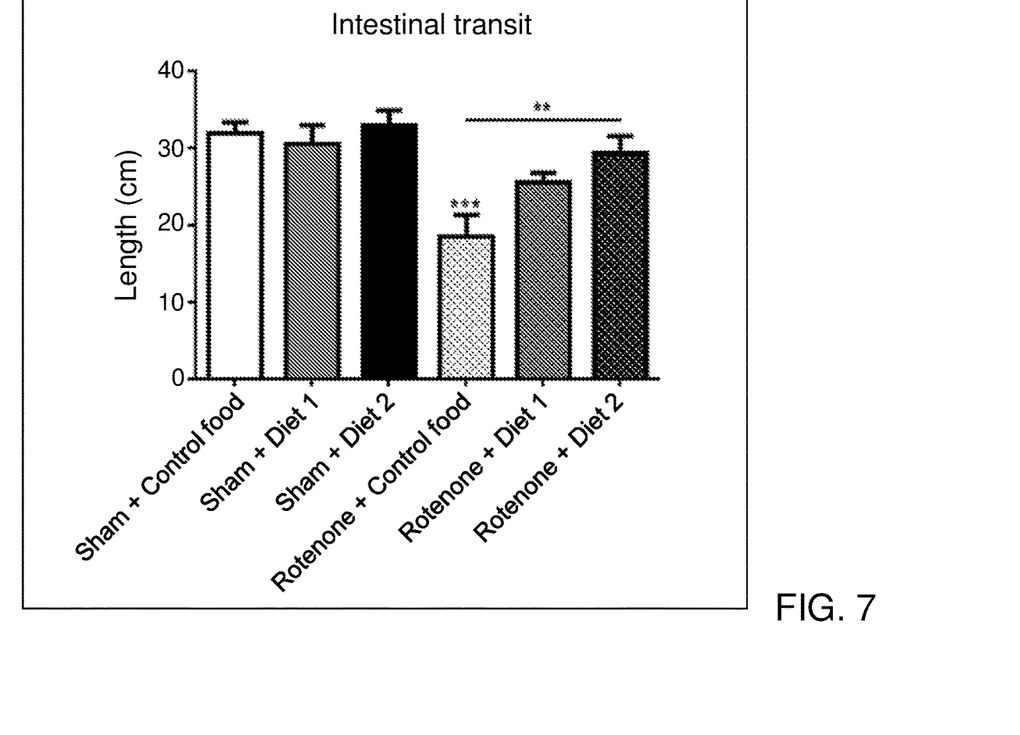
FIG. 7 shows an effect of Diets 1 and 2 on intestinal transit.
Figure 8:
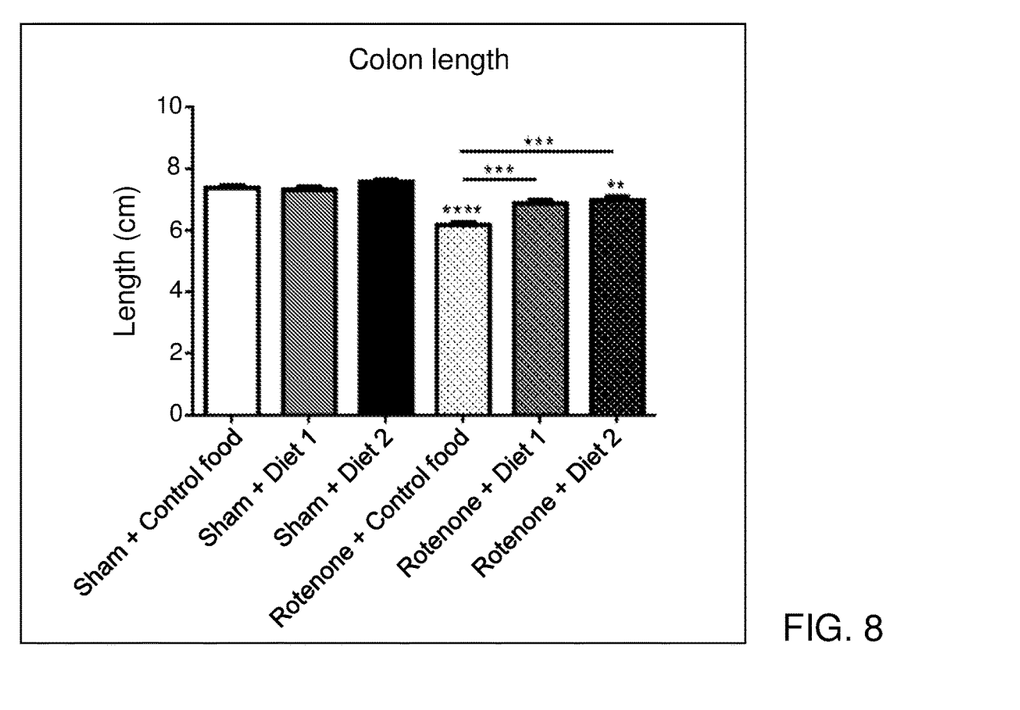
FIG. 8 shown an effect of Diets 1 and 2 on colon length.

A rotarod test was performed for 10 weeks, starting 1 week after intra-striatal injection with rotenone or sham (vehicle). As shown in FIG. 6, rotenone induced motor problems, but after start of treatment with Diet 1 or Diet 2, an improvement in motoric functioning was shown (increased average time on the rod, compared to the 'Rotenone+Control Food' group). The additional presence of the dietary fibre had an positive effect on motoric functioning FIGS. 7 and 8 show an effect of Diets 1 and 2 on intestinal transit and colon length.

The invention claimed is:

1. A method for the treatment of constipation comprising administering a combination of a pyrimidine derivative and at least one polyunsaturated fatty acid having 18-24 carbon atoms selected from the group consisting of docosahexaenoic acid (DHA) and eicosapentaenoic acid (EPA) to an individual in need of such treatment, wherein the daily dosage of DHA plus EPA administered via the combination is in the range of 1000 mg to 5000 mg.

2. The method according to claim 1, wherein the constipation is slow transit constipation.

3. The method according to claim 1, wherein the constipation is associated to a gastrointestinal disorder.

4. The method according to claim 3, wherein the gastrointestinal disorder is a chronic inflammation of the mucosa of the gastrointestinal tract.

5. The method according to claim 1, wherein the constipation is associated to a neurological disorder or a psychiatric disorder.

6. The method according to claim 5, wherein the neurological disorder is a peripheral neuropathy, an autonomic neuropathy, or an enteric nervous system neuropathy.

7. The method according to claim 5, wherein the neurological disorder is selected from the group consisting of synucleopathies, diabetic neuropathy, cerebrovascular disease, cerebral palsy, Parkinson's disease, Duchenne's dystrophy, cerebrovascular disease, Multiple Sclerosis, pure autonomic failure, and spinal cord injury.

8. The method according to claim 5, wherein the neurological disorder is spinal cord injury.

9. The method according to claim 5, wherein the neurological disorder is Parkinson's disease.

10. The method according to claim 5, wherein the neurological disorder is stroke.

11. The method according to claim 5, wherein the neurological disorder is cerebral palsy.

12. The method according to claim 5, wherein the psychiatric disorder is pervasive development disorder, or the psychiatric disorder is depression.

13. The method according to claim 1, wherein the polyunsaturated fatty acid comprises docosahexaenoic acid (DHA) and eicosapentaenoic acid (EPA).

14. The method according to claim 13, wherein the daily dosage of DHA administered via the combination is in the range of 300 mg to 4000 mg.

15. The method according to claim 1 comprising a fish oil providing polyunsaturated fatty acid having 18-24 carbon atoms.

16. The method according to claim 1, wherein the pyrimidine derivative is a nucleobase, a nucleoside or a nucleotide.

17. The method according to claim 1, wherein the pyrimidine derivative is selected from the group consisting of uridine, deoxyuridine, derivatized uredines, derivatized deoxyuridines, cytidine, deoxycytidine, derivatized cytidines and derivatised deoxycytidines.

18. The method according to claim 1, wherein the pyrimidine derivative is a nucleotide, of which nucleotide one or more functional groups may be derivatized.

19. The method according to claim 18, wherein the nucleotide is selected from the group consisting of UMP, UDP, UTP, CMP, CDP, CTP dUMP, dUDP, dUTP, dCMP, dCDP and dCTP, wherein optionally one or more hydroxyl moieties of the (deoxy)ribose of said nucleotide is acylated.

20. The method according to claim 19, wherein the nucleotide is UMP or acylated UMP.

21. The method according to claim 17, wherein the combination comprises uridine or acylated uridine.

22. The method according to claim 1, wherein the combination is to be administered to a human of at least 18 years of age.

23. The method according to claim 1, wherein the combination is to be administered as part of a nutritional composition.

24. The method according to claim 23, wherein the combination is a nutritional composition comprising choline.

25. The method according to claim 23, wherein the combination further comprises at least one of phospholipids, vitamin E, vitamin C, selenium, vitamin B12, vitamin B6 or folic acid.

26. A method for monitoring the treatment of constipation comprising administering a combination of a pyrimidine derivative and a polyunsaturated fatty acid having 18-24 carbon atoms, wherein the polyunsaturated fatty acid comprises at least one polyunsaturated fatty acid selected from the group consisting of docosahexaenoic acid (DHA) and eicosapentaenoic acid (EPA), and wherein the daily dosage of DHA plus EPA administered via the combination is in the range of 1000 mg to 5000 mg, and measuring the level of alpha-synuclein aggregates in the colon.

27. A method for monitoring the treatment of synucleopathies, comprising administering a combination of a pyrimidine derivative and a polyunsaturated fatty acid having 18-24 carbon atoms, wherein the polyunsaturated fatty acid comprises at least one polyunsaturated fatty acid selected from the group consisting of docosahexaenoic acid (DHA) and eicosapentaenoic acid (EPA), and wherein the daily dosage of DHA plus EPA administered via the combination is in the range of 1000 mg to 5000 mg, and measuring the level of alpha-synuclein aggregates in the colon.

28. A method for the treatment of constipation comprising administering a combination of a pyrimidine derivative and a polyunsaturated fatty acid having 18-24 carbon atoms to an individual in need of such treatment, wherein the polyunsaturated fatty acid is selected from the group consisting of docosahexaenoic acid (DHA), and wherein the daily dosage of DHA administered via the combination is in the range of 1000 mg to 4000 mg.

* * * * *